US00PP12289P2

(12) United States Plant Patent
Sharma

(10) Patent No.: US PP12,289 P2
(45) Date of Patent: Dec. 18, 2001

(54) NEW GUINEA IMPATIENS PLANT NAMED 'OVATION SALMON'

(75) Inventor: Jagan N. Sharma, San L. Obispo County, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/550,519

(22) Filed: Apr. 17, 2000

(51) Int. Cl.[7] ..... A01H 5/00

(52) U.S. Cl. ..... Plt./318

(58) Field of Search ..... Plt./318

*Primary Examiner*—Bruce R. Campell
*Assistant Examiner*—Anne Marie Grünberg
(74) *Attorney, Agent, or Firm*—Webb Ziesenheim Logsdon Orkin & Hanson, P.C.

(57) ABSTRACT

A distinct cultivar of Impatiens plant named Ovation Salmon, characterized by its salmon-orange flower color, large flower diameter, bright green leaves, continuous, and long-lasting flowering, self-branching and vigorous habit.

1 Drawing Sheet

The present invention relates to a new and distinctive cultivar of Impatiens plant. botanically known as *Impatiens hawkeri*, commercially known as New Guinea Impatiens, and known by the cultivar name 'Ovation Salmon'. Ovation Salmon was developed in a controlled breeding program by crossing Waller Seedling No. 96-2G-50-1 (seed parent) with Waller Seedling No. 93-1G-750 (pollen parent). The seed and pollen parents are proprietary breeding lines which have not been sold or made publicly available in this country.

Asexual reproduction carried out by the inventor in Lompoc, Calif. by terminal or stem cuttings has shown that the unique features of this new Impatiens are stabilized and are reproduced true to type in successive propagations.

The following combination of characteristics distinguishes the new Impatiens from both its parent varieties and other cultivated Impatiens of this type known and used in the floriculture industry:

1. Ovation Salmon flowers are salmon-orange colored of Orange-Red Group 33A, as compared to Harmony Deep Salmon (unpatented), which is Red Group 40A, and Celebration Salmon (U.S. Plant Pat. No. 8,870), which is Red Group 52A.

2. Ovation Salmon has a similar flower diameter size as Harmony Deep Salmon (6.5 to 7.0 cm) and is smaller than Celebration Salmon (7.0 to 7.5 cm).

3. Ovation Salmon has smaller leaves (9 to 10 cm) than Harmony Deep Salmon and Celebration Salmon (11 to 12 cm).

4. Ovation Salmon is similar in height to Harmony Deep Salmon but more compact growing than Celebration Salmon.

5. Ovation Salmon has bright green leaves while Harmony Deep Salmon has dark green leaves and Celebration Salmon has medium green leaves with some cream variegation.

6. Ovation Salmon has red-purple pedicels while both Harmony Deep Salmon and Celebration Salmon have yellow-green pedicels.

7. Ovation Salmon has red-purple spurs with red-purple tips while Harmony Deep Salmon and Celebration Salmon have red-purple spurs with green tips.

8. Ovation Salmon has red-purple stems while Harmony Deep Salmon and Celebration Salmon have green stems.

9. Ovation Salmon has a red-purple midrib and green veins on the underside of the leaves, while Harmony Deep Salmon has red-purple veins and midribs, and Celebration Salmon has green veins and midrib on the underside of the leaves.

The accompanying colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. Fertilizer regime is 200 ppm $N_2$, 75 ppm K, and 200 ppm P, with trace elements added, constant feed. The plants were grown at 16° C. night temperatures, under 3000 to 4000 foot candles of light and with nutritional trace elements added. Habit of growth, foliage coloration, leaf variegation, size of leaves and flower size will be greatly influenced by nutritional and environmental conditions.

Color references are made to The Royal Horticultural Society Colour Chart except where general terms of ordinary significance are used.

Parentage: A controlled cross between female parent, Waller Seedling No. 96-2G-50-1 and male parent Waller Seedling No. 93-1G-750.

Propagation:

(*A*) *Type cutting.*—Stem tip 15 mm long will develop to 4 to 5 cm long in 18 to 21 days.

(*B*) *Time to root.*—8–10 days at 23° C. summer; 10–12 days at 20° C. winter.

(*C*) *Rooting habit.*—Heavy, fibrous.

Plant description:

(*A*) *Form and habit of growth.*—Mounded to semi-upright, self-branching, intermediate in height, flowers open over the top of leaf canopy; continuous flowering; vigorous growing flowering herb. Average height is 20 to 25 cm and average width is 35 to 40 cm. Internode length is 4 to 5 cm but is highly variable. Pedicel is Greyed-Purple Group 184B, stem is Yellow-Green Group 147C with a Greyed-Purple Group 185C cast, and internode is Yellow-Green Group 147C with a Greyed-Purple Group 185C cast changing to Greyed-Purple Group 185D near the node. Pedicel length is 3.5 cm.

(*B*) *Foliage description.*—Deep green; light green midrib on top side of the leaf and red-purple on the underside; no leaf variegation. (1) Size: 9 to 10 cm long and 3.0 to 3.5 cm wide on average mature leaf. (2) Shape: Lanceolate with acuminate apex and acute base. (3) Texture: Both upper and lower surfaces are glabrous. (4) Margin: Entire, with fine cilia. (5) Color: Young foliage, top side is Yellow-Green Group 146A, underside is Yellow-Green Group 147B. Mature foliage, top side is Yellow-Green Group 147A, underside is Yellow-Green Group 147B. (6) Venation: Pinnate, upper side is Yellow-Green Group 147C, and lower side is Greyed-Purple Group 184C. (7) upper midrib is Yellow-Green Group 147C with a Greyed-Purple Group 184C cast, and lower midrib is Greyed-Purple Group 184C.

(*C*) *Branching.*—The branching is naturally occurring. Lateral branching at base: 10 or more lateral branches starting at the base and then from each leaf whorl. The age of the plant will determine the number of lateral branches. Lateral branch length is 10 to 15 cm but is highly variable.

Flowering description:

(*A*) *Flowering habits.*—Flowers continuously from leaf whorl in a progressively orderly manner with one flower per leaf axil. When the last flower in a whorl opens, the first flower in the leaf whorl above starts to open. It takes 5 to 7 days for a mature bud to fully open and the flower may last two weeks or longer depending on the environment. The time to first flower is approximately 8 weeks from root cuttings. The flowers are self-cleaning.

(*B*) *Natural flowering season.*—Indeterminate and continuous; quantity of flowering increases with increasing levels of light.

(*C*) *Flower bud.*—Ellipsoidal; flowers perfect; spur is 5.0 cm long on mature bud with the throat behind the ovary and originating from the major sepal. Bud length is 18 to 20 mm and bud diameter is 12 to 14 mm. Spur is Red-Purple Group 60B, spur tip is Red-Purple Group 60A, and flower bud is Orange-Red Group 33A just before opening.

(*D*) *Flowers borne.*—On individual light red-purple cast pedicels 3.0 cm long from a whorl of usually five leaves. Flowering progressively around the whorls as buds and leaves develop. Leaf axils have one flower each.

(*E*) *Quantity of flowers.*—Numerous because of self-branching nature of plant and the long-lasting flower characteristic.

(*F*) *Diameter of flower.*—6.5 to 7.0 cm.

*Flower depth.*—6 mm.

(*G*) *Petals.*—(1) Shape: Heart, keel petals are the largest. (2) Color: Top side in winter when opening is Orange-Red Group 33A, without fading; underside is Orange-Red Group 35B. (3) Number of petals: Five. (4) Size of petals: Standard: 4.0 cm wide and 3.0 cm long, two equal lobes with a moderate cut. Wings: 3.0 cm wide and 3.0 cm long, two unequal lobes with shallow cut. Keel: 4.0 cm wide and 3.5 cm long, two unequal lobes with moderate cut.

(*H*) *Reproductive organs.*—(1) Stamens: Five in number. (a) Anther: Hooded shape, color is Yellow-White Group 158B with a heavy Red Group 42A cast. (b) Pollen color: Yellow-White Group 158C. Pistils: (a) Stigma: Five, segmented column, color is White Group 155B. (b) Style color: White Group 155B. (c) Ovaries: Five in number, size is 7 mm when immature, color is Yellow-Green Group 146A.

(*I*) *Fertility.*—The plants are fertile, but do not normally set seed under greenhouse or garden conditions, unless in a controlled crossing program.

Disease resistance: No significant disease or insect problems seen to date.

OTHER IMPORTANT CHARACTERISTICS

1. Self-branching, early flowering nature allows cultivar to be grown in 10 cm pots but is also very vigorous enough to be grown in 15 to 25 cm containers as well.

2. Minimal fading of older flowers and large overlapping petals result in a round flower that produces an attractive floral display.

3. Has shown the ability tolerate both high temperatures and full sun and continue to bloom as demonstrated in Connellsville, Pa. summer trials and to bloom as well with cool night temperatures (5 to 10° C.) as demonstrated in outdoor trials in Lompoc, Calif., thus, extending the growing season.

I claim:

1. A new and distinct variety of Impatiens plant named Ovation Salmon, as illustrated and described.

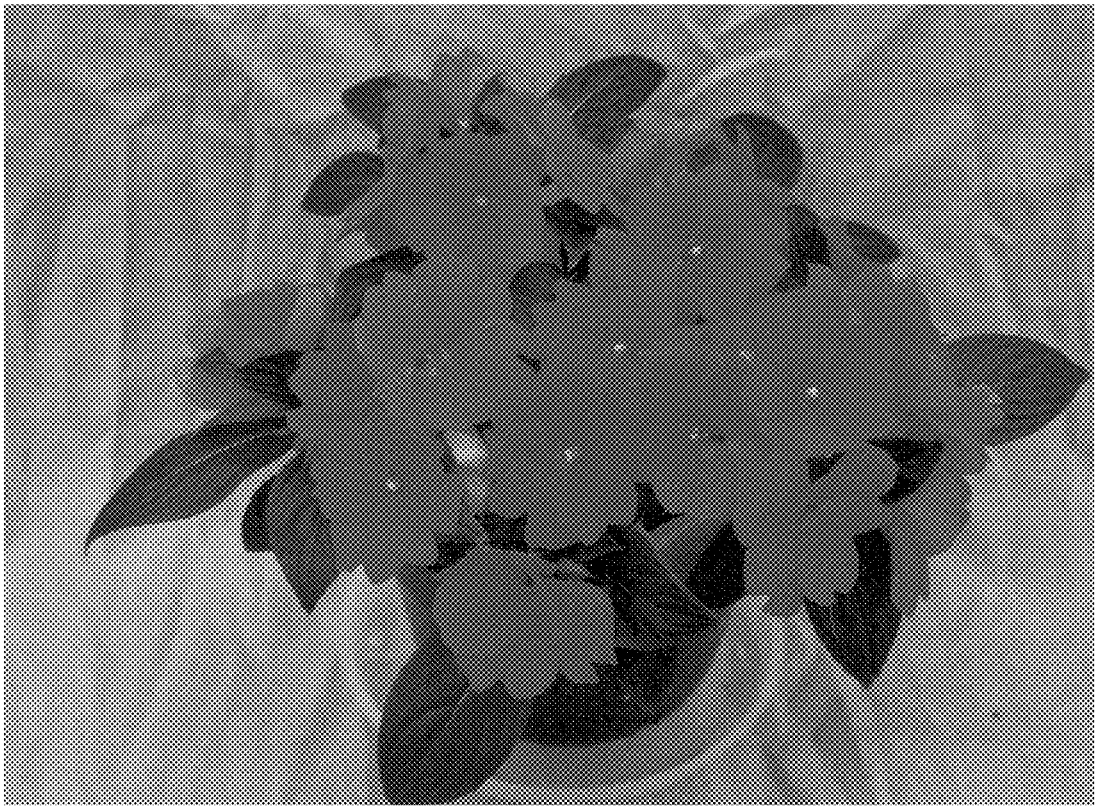

* * * * *